United States Patent [19]
Sumiya

[11] Patent Number: 5,637,109
[45] Date of Patent: *Jun. 10, 1997

[54] APPARATUS FOR OPERATION ON A CORNEA USING LASER-BEAM

[75] Inventor: Toshifumi Sumiya, Nukata-gun, Japan

[73] Assignee: Nidek Co., Ltd., Aichi, Japan

[*] Notice: The portion of the term of this patent subsequent to Feb. 7, 2015, has been disclaimed.

[21] Appl. No.: 219,412

[22] Filed: Mar. 29, 1994

Related U.S. Application Data

[63] Continuation of Ser. No. 15,922, Feb. 10, 1993, abandoned.

[30] Foreign Application Priority Data

Feb. 14, 1992 [JP] Japan ..................... 4-061211
Sep. 30, 1992 [JP] Japan ..................... 4-286998
Sep. 30, 1992 [JP] Japan ..................... 4-286999

[51] Int. Cl.$^6$ ............... A61B 17/00; A61N 5/06
[52] U.S. Cl. ........................ 606/5; 606/4
[58] Field of Search ................. 606/4, 5, 6, 10, 606/11, 13

[56] References Cited

U.S. PATENT DOCUMENTS 4,370,540  1/1983  Davis et al. ................ 219/121.6
4,732,148  3/1988  L'Esperance, Jr. ................ 606/4
4,911,711  3/1990  Telfair et al. ................ 606/4
5,102,409  4/1992  Balgorod ................ 606/13
5,108,388  4/1992  Trokel ................ 606/13
5,163,934  11/1992  Munnerlyn ................ 606/13

*Primary Examiner*—Stephen C. Pellegrino
*Assistant Examiner*—Sonya Harris-Ogugua
*Attorney, Agent, or Firm*—Finnegan, Henderson, Farabow, Garrett & Dunner, L.L.P.

[57] ABSTRACT

An apparatus for ablating the surface of the cornea using a laser beam to correct the refractive of an eye to be operated having a laser source for emitting a laser beam having a non-uniform intensity distribution of Gaussian distribution and the like to one direction and a uniform beam intensity in another direction, an ablation optical system for ablating the surface of the cornea by the laser beam emitted from the laser source, translational scanning device for scanning the laser beam in the direction of non-uniform intensity distribution, beam rotating device for rotating the laser beam emitted from the laser source round the optical axis in the ablation optical system, control device which controls the beam rotation by the beam rotating device whenever the laser beam is scanned in parallel by the scanning device.

19 Claims, 13 Drawing Sheets

Related Art

FIG. 5
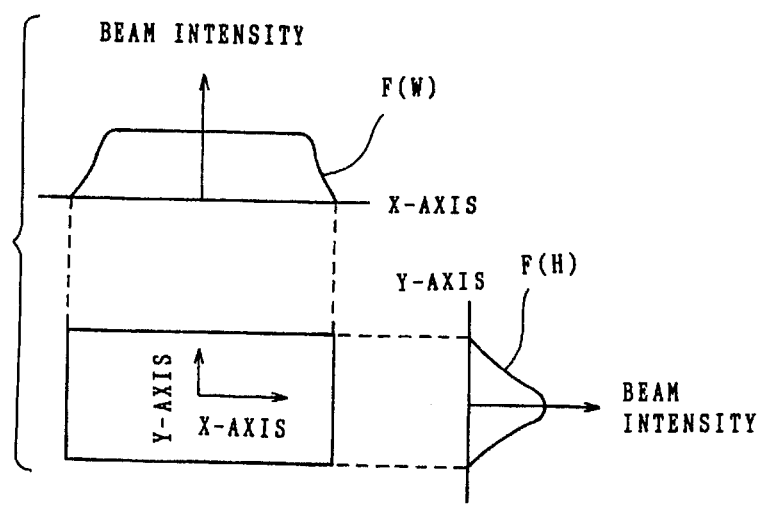
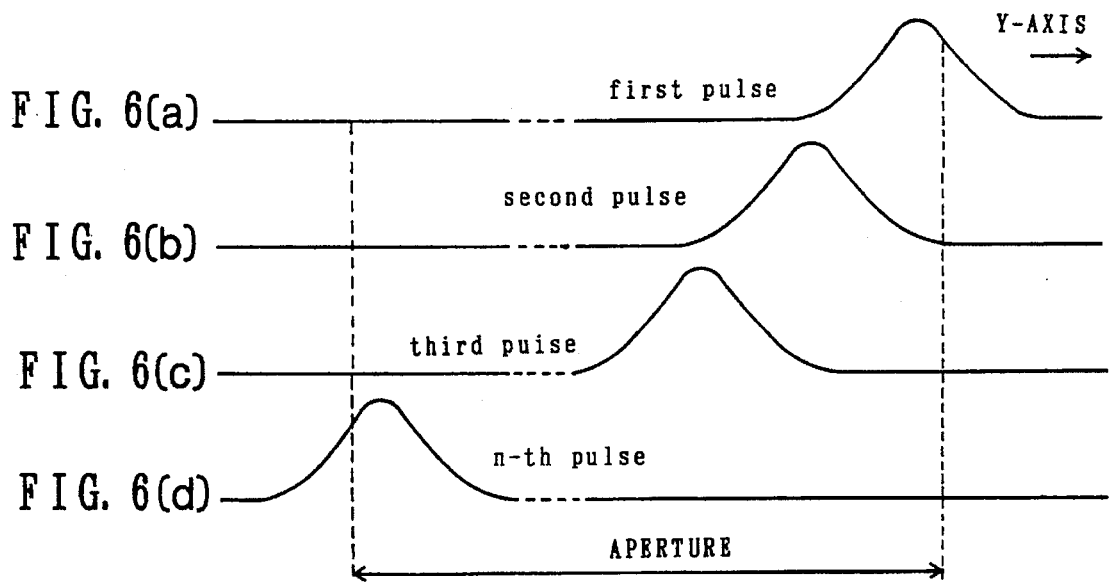
FIG. 6(a) first pulse
FIG. 6(b) second pulse
FIG. 6(c) third pulse
FIG. 6(d) n-th pulse
APERTURE

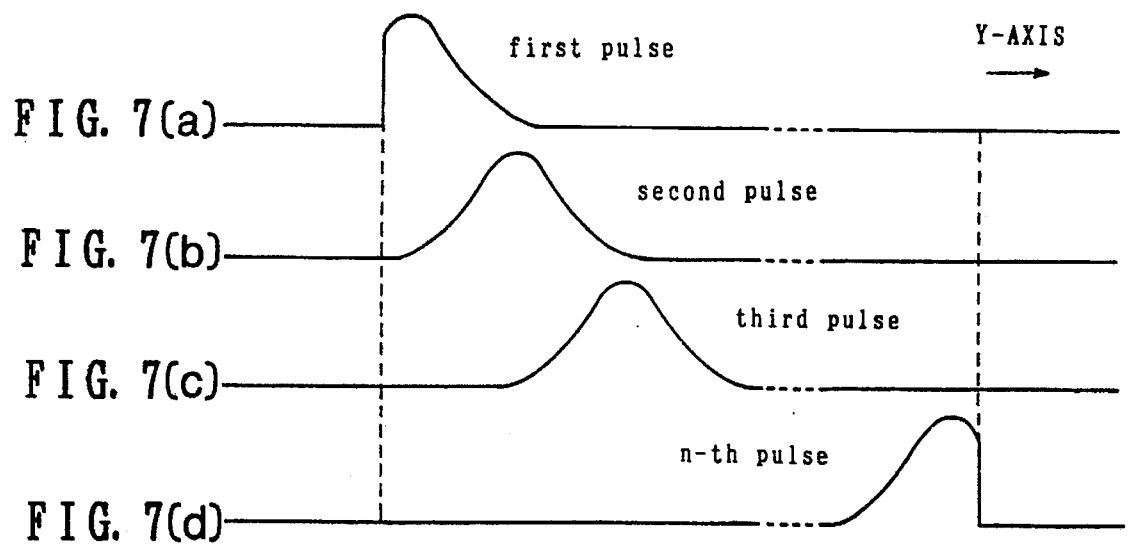
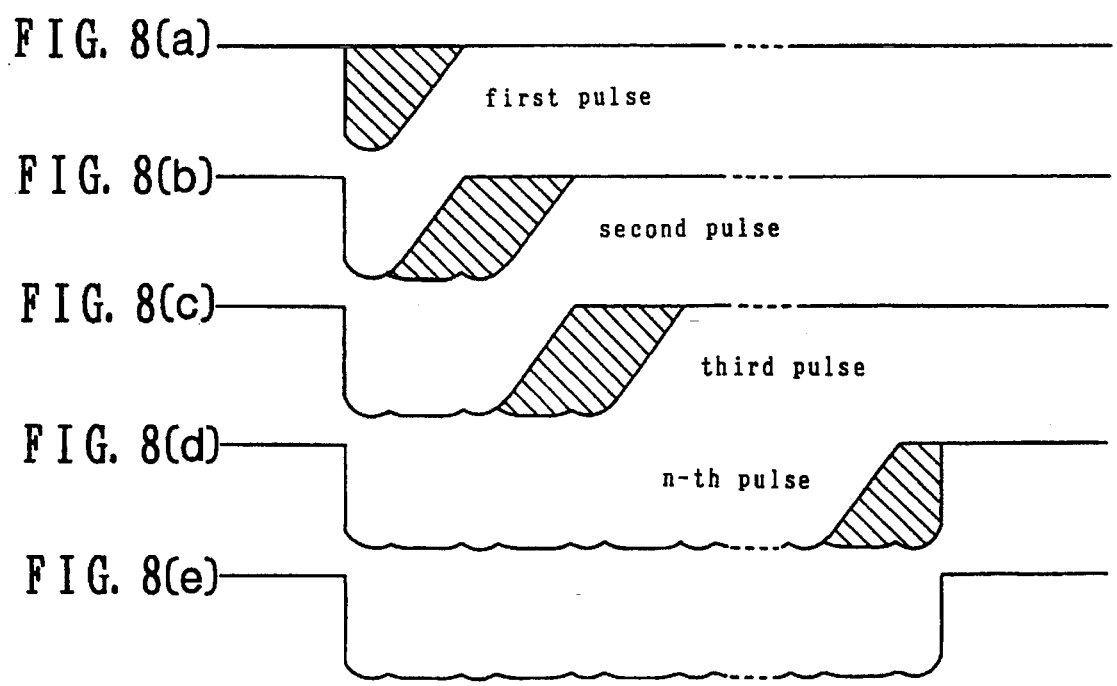

APPARATUS FOR OPERATION ON A CORNEA USING LASER-BEAM

This application is a continuation, of application Ser. No. 08/015,922, filed Feb. 10, 1993, now abandoned.

BACKGROUND OF THE INVENTION

1. Field of the Invention

The present invention relates to an apparatus for operation on a cornea using laser-beam to correct a refraction error of an eye by excising a surface of the cornea of an eye. More particularly, the present invention relates to an ablation apparatus for ablating an object by laser beam (typically an excimer laser) having a non-uniform beam intensity of Gaussian distribution in one direction and a uniform beam intensity in the vertical direction, and an apparatus for correcting the myopic astigmatism of an eye.

2. Description of Related Art

Recently, a method has been executed for correcting the refraction of an eye by ablating the surface of the cornea to change the curvature of the cornea, e.g. Photorefractive Keratectomy (PRK). In this method, it is necessary to control the depth of the ablation area so that it is uniform. Japanese Patent Application No. HEI 2-416767 (U.S. application Ser. No.812,819), the title is ABLATION APPARATUS FOR ABLATING AN OBJECT BY LASER-BEAM, filed by this applicant proposes the method for ablating an object in uniform depth by translational scanning the laser beam having a uniform beam intensity in one direction and a non-uniform beam intensity of Gaussian distribution in the vertical direction, e.g., an excimer laser beam, into the non-uniform beam intensity distribution direction.

Another method has also been proposed for correcting the refraction error of an eye. Specifically, in this method, the myopia is corrected by excising a cornea so that an ablation area forms a convex lens appearance as shown in FIG. 1 by gradually changing a diameter of a circular variable diaphragm so as to extend its size from small to larger, or to reduce from large to smaller. The astigmatism is corrected by excising the cornea so as to form a cylindrical lens appearance as shown in FIG. 2 by gradually changing a width of a variable slit the same as above.

However, there are some problems with the methods mentioned above. In the former method employing a laser beam which has a uniform beam intensity in one direction and a non-uniform beam intensity of Gaussian distribution in the vertical direction, the ablated area of the cornea can not have a uniform depth unless the laser beam has an almost uniform beam intensity in one direction. Due to the insufficiency of the alignment of the laser beam resonator, the uniformity of the laser beam emitted from a laser source is different between each laser oscillator. When beam intensity distribution in a direction to be uniform is not uniform so that it cannot be disregarded as reference to FIG. 3, and although the depth of ablation in a scanning direction can be uniform, a non-uniform beam intensity distribution remains in the vertical direction, therefore, a uniform depth in a whole ablation area can not be obtained.

Additionally, there is a similar problem as that mentioned above when beam intensity on a surface of an object is non-uniform due to problems in the optical system for transferring the laser beam into an object to be ablated.

In the latter method of changing a diameter of a variable diaphragm or variable slit, it is necessary to confine the irradiation area by employing a circular variable diaphragm when correcting the myopia, or by employing a variable slit when correcting the astigmatism. Therefore, the structure is complex and its operation becomes complicated. When correcting myopic astigmatism, it is necessary to repeat operations for correcting with different diaphragms, that is, correcting the astigmatism by using a variable slit after correcting the myopia by using a circular variable diaphragm, or in reverse order.

SUMMARY OF THE INVENTION

Accordingly, it is an object of the present invention to overcome the above problems and to provide an apparatus for ablating an object by translational scanning the laser beam, whereby the object could be ablated in a uniform depth even if the beam intensity distribution of the laser beam in a direction to be uniform is not uniform.

It is a further object to provide an apparatus by which both the myopia and the astigmatism can be corrected in one operation, if it is necessary to confine each irradiation area.

The above and further objects and novel features of the invention will be attained by an apparatus for operation on a cornea using a laser beam to correct the refractive error of an eye. The apparatus comprises a laser source for emitting a laser beam having a non-uniform intensity distribution of Gaussian distribution and the like in one direction and a uniform beam intensity in another direction, an optical system for ablating the surface of a cornea of the eye to be operated by irradiating the laser beam emitted from the laser source, translational scanning means for scanning the laser beam in the direction of non-uniform intensity distribution of the laser beam irradiated on the surface of a cornea in the optical system for ablation, beam rotating means for rotating the laser beam emitted from the laser source round the optical axis in the ablation optical system for ablation, control means for controlling the beam rotation by the beam rotating means whenever the laser beam is scanned in parallel by the scanning means.

To achieve the objects, in another invention, an apparatus for operation on the cornea using a laser beam to correct the refractive of an eye to be operated comprises a laser source for emitting a laser beam, an ablation optical system for irradiating the laser beam emitted from the laser source onto the cornea of an eye to be operated, circular diaphragm, arranged in the ablation optical system, for confining the ablation area on the cornea, diaphragm rotating means for rotating the diaphragm round the optical axis, changing means for changing an aperture diameter of the diaphragm, diaphragm inclining means for inclining the circular diaphragm to the optical axis of the laser beam.

BRIEF DESCRIPTION THE DRAWINGS

The invention will be described in detail with reference to the following drawings, wherein:

FIG. 5 is a schematic diagram of a horizontal (X-axis) beam intensity profile and a vertical (Y-axis) beam intensity of a laser beam from an excimer laser as used in the embodiment of FIG. 4;

Figure 4:
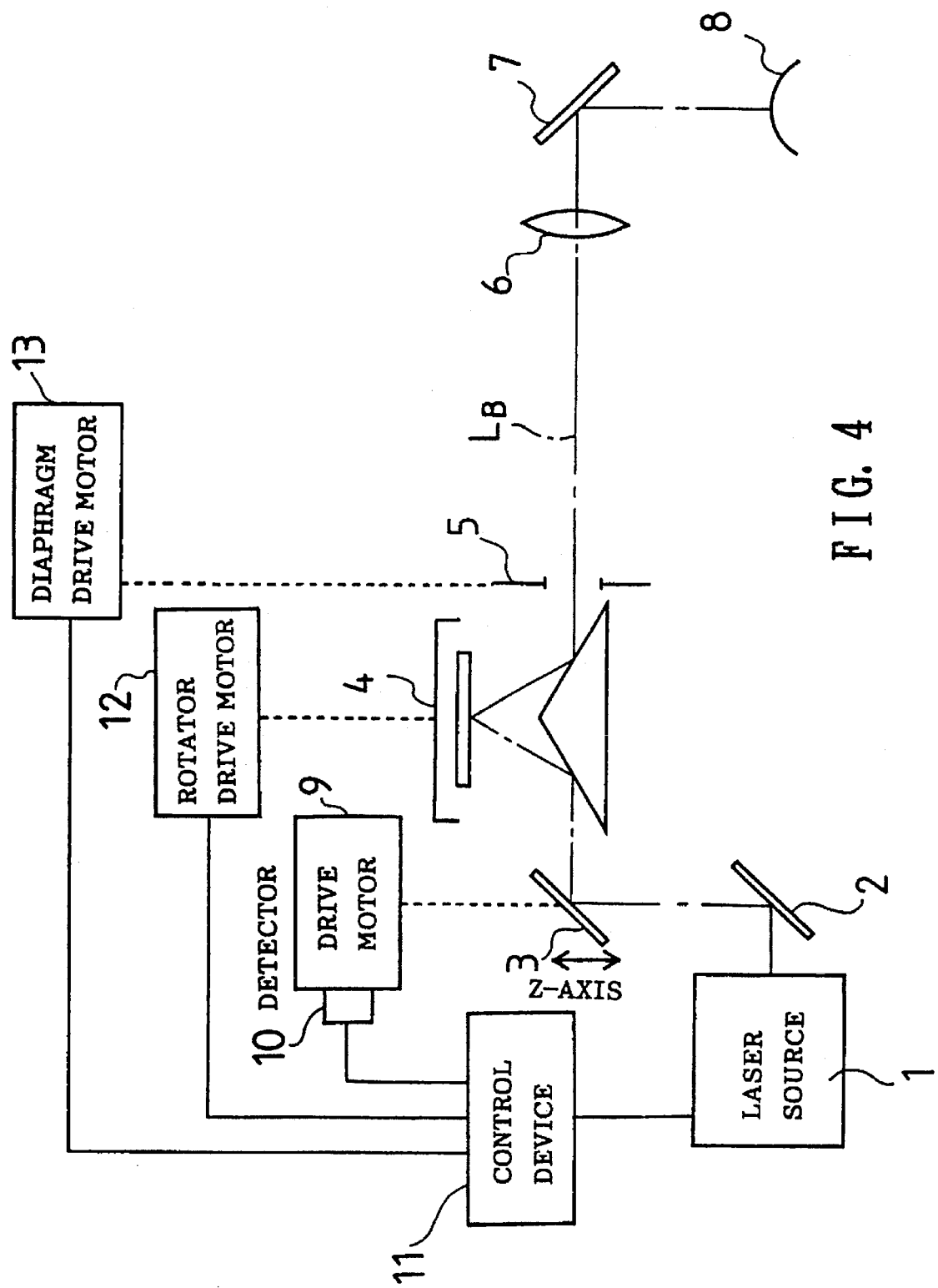
FIG. 4 is a schematic diagram of the arrangement of components of the first embodiment embodying the present invention.
Figure 9A:
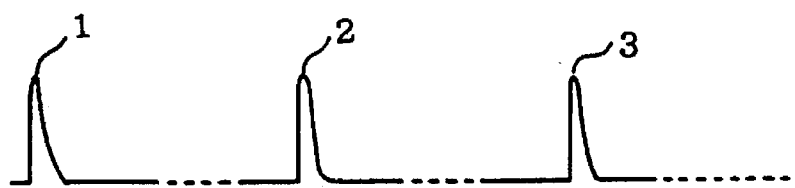
Figure 9B:
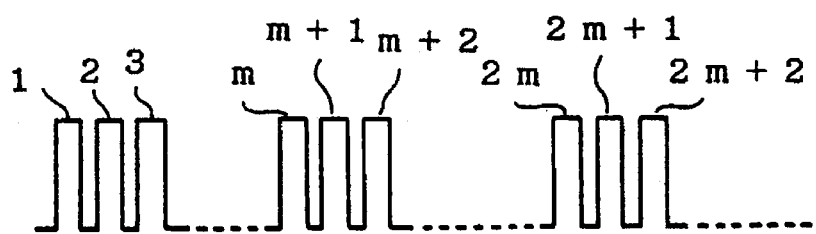
Figure 10:
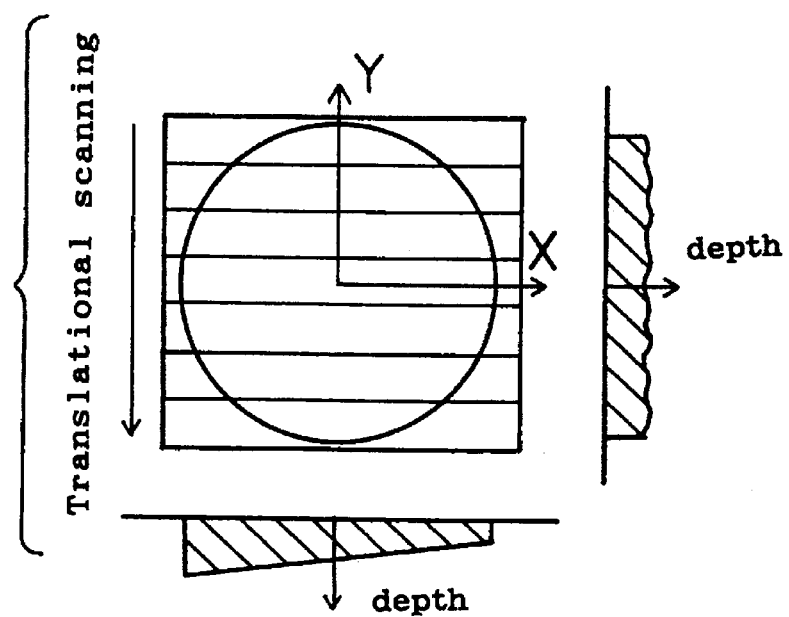
Figure 11:
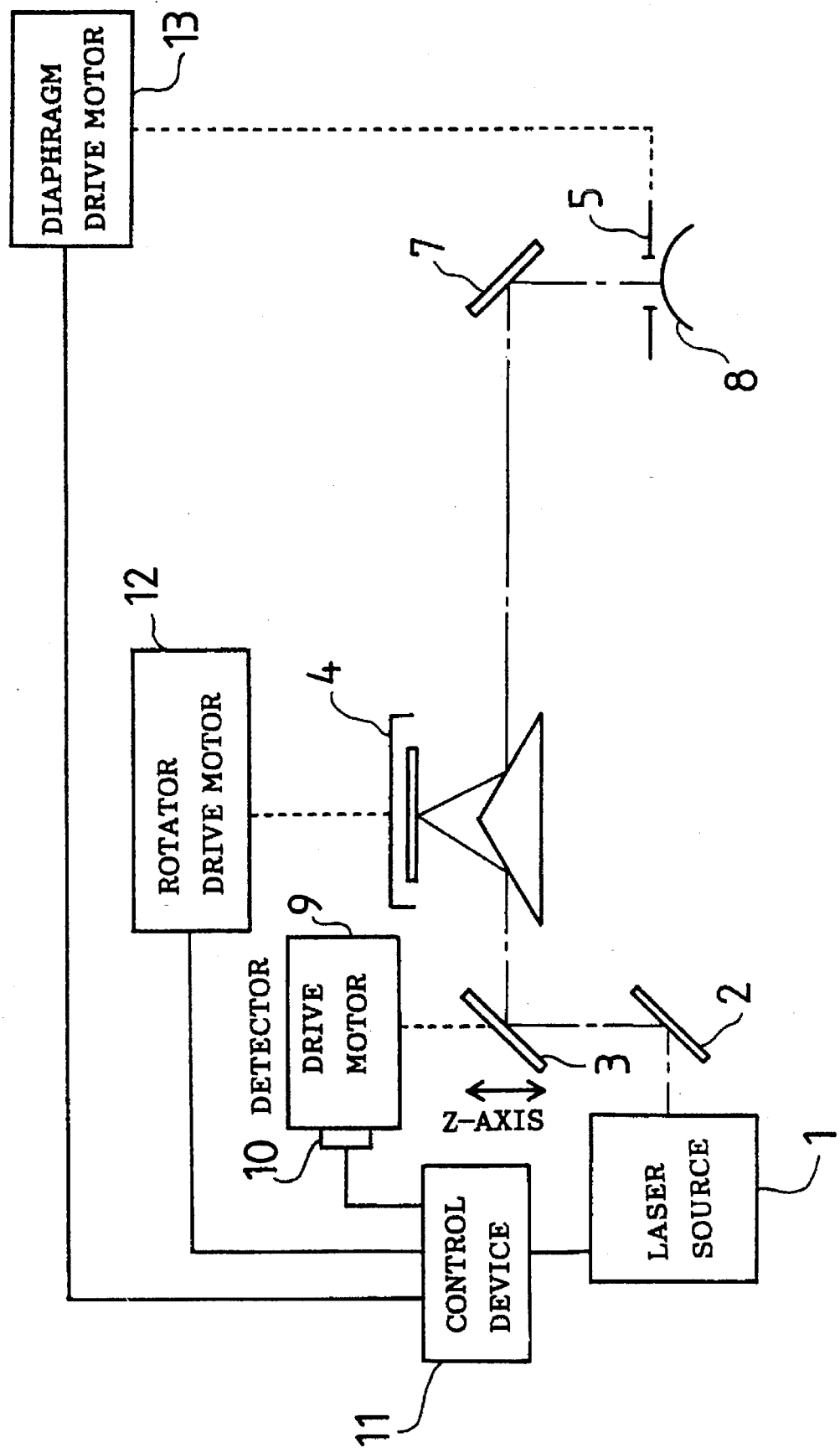
Figure 12:
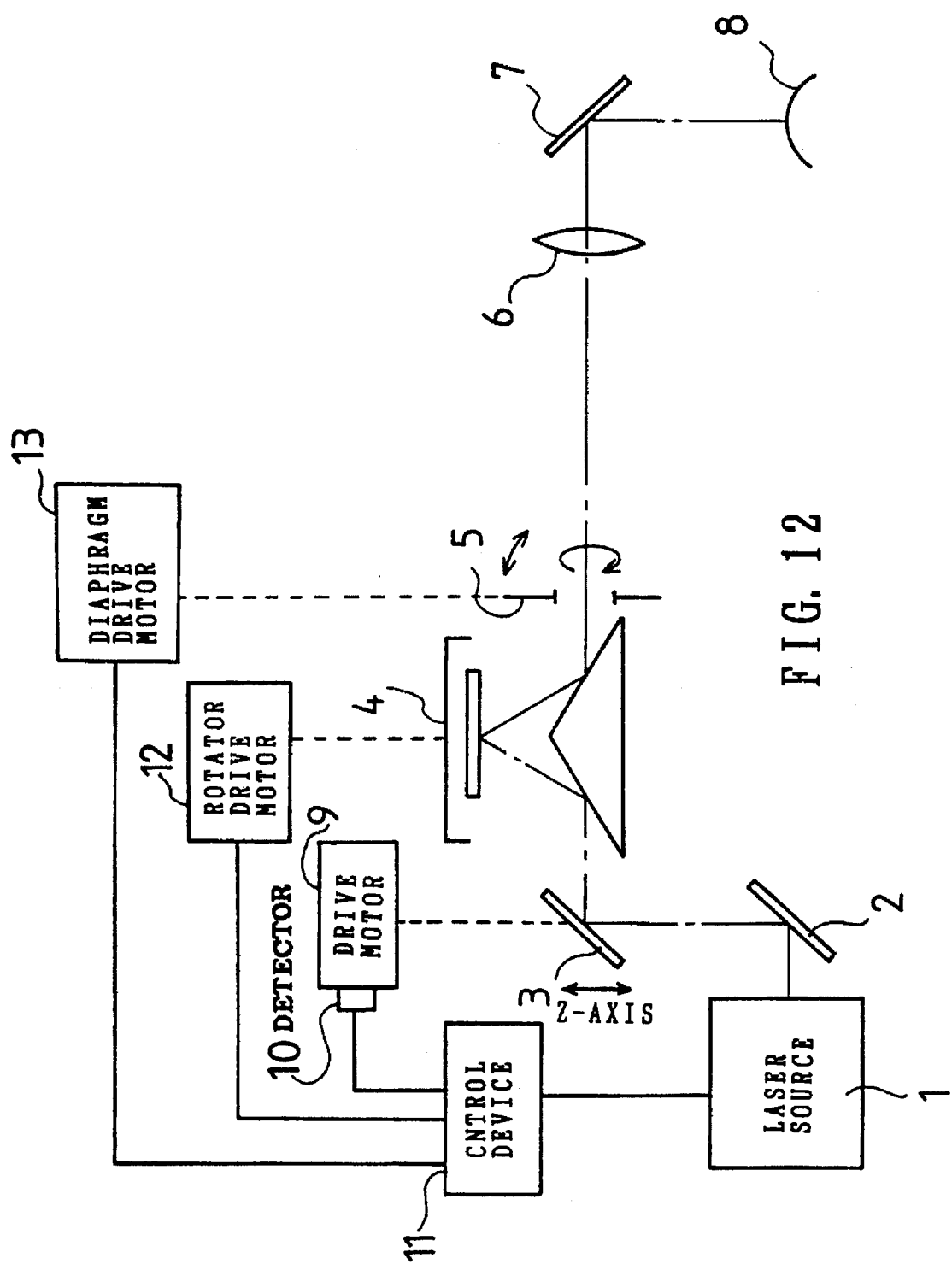
Figure 13:
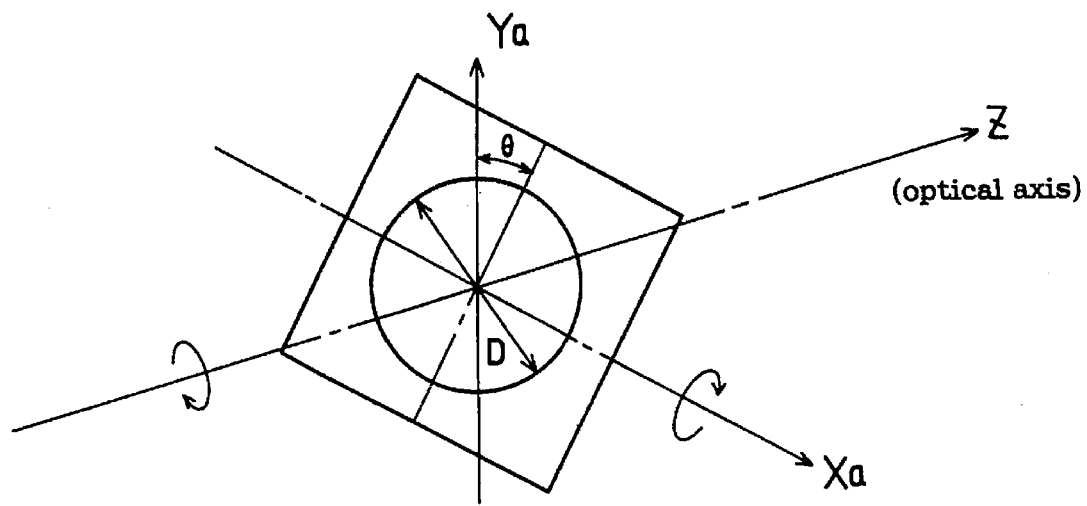
Figure 14:
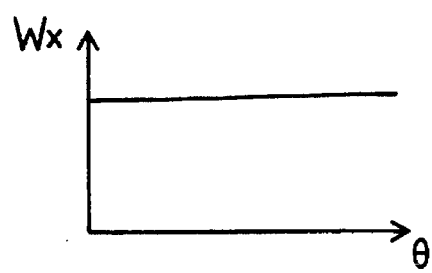
Figure 15:
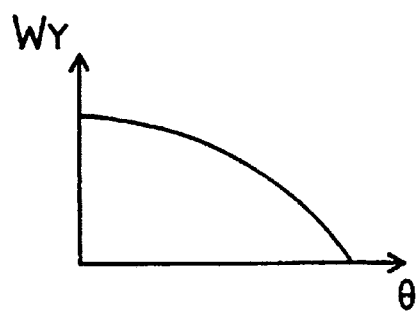
Figure 16:
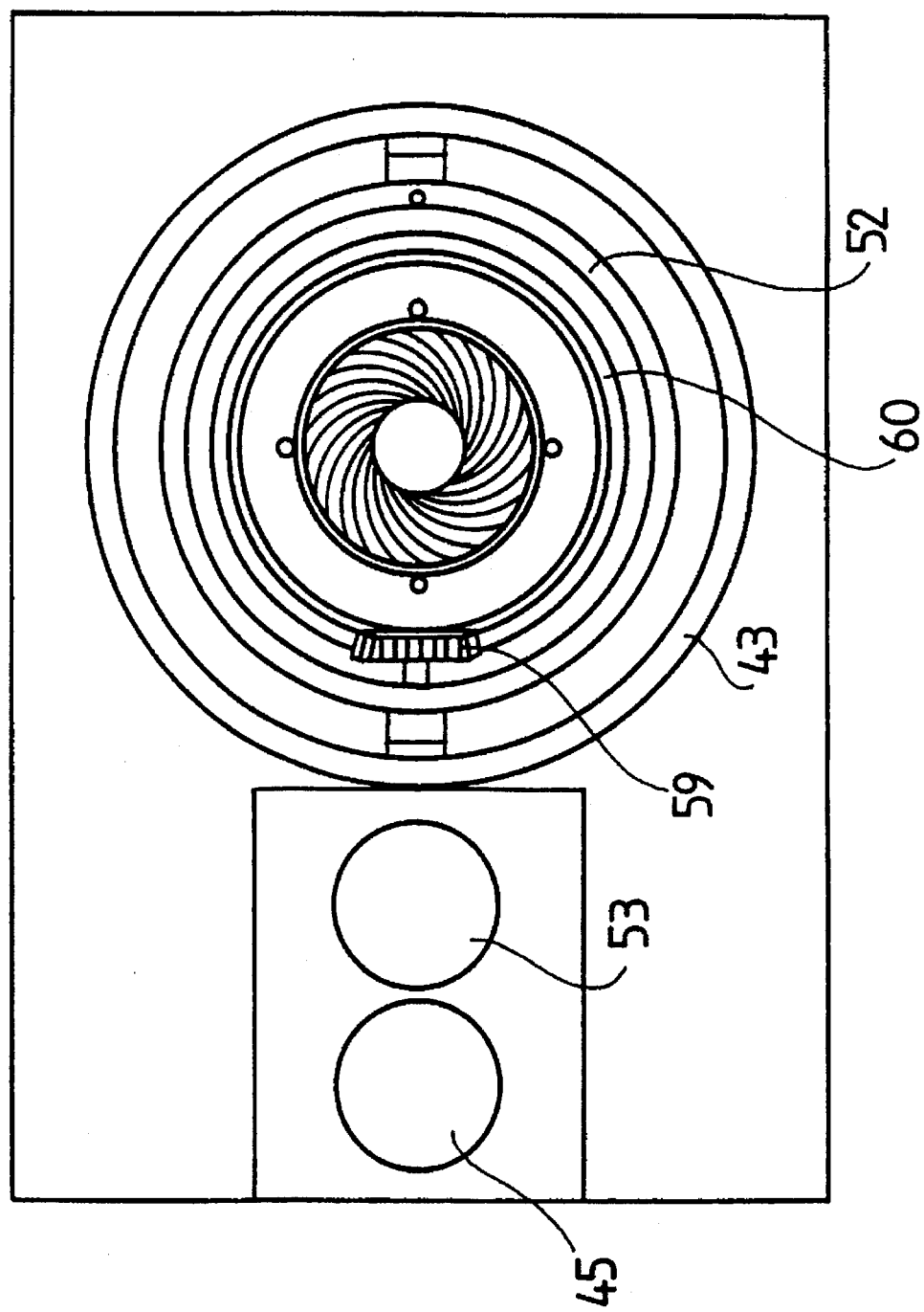
Figure 17:
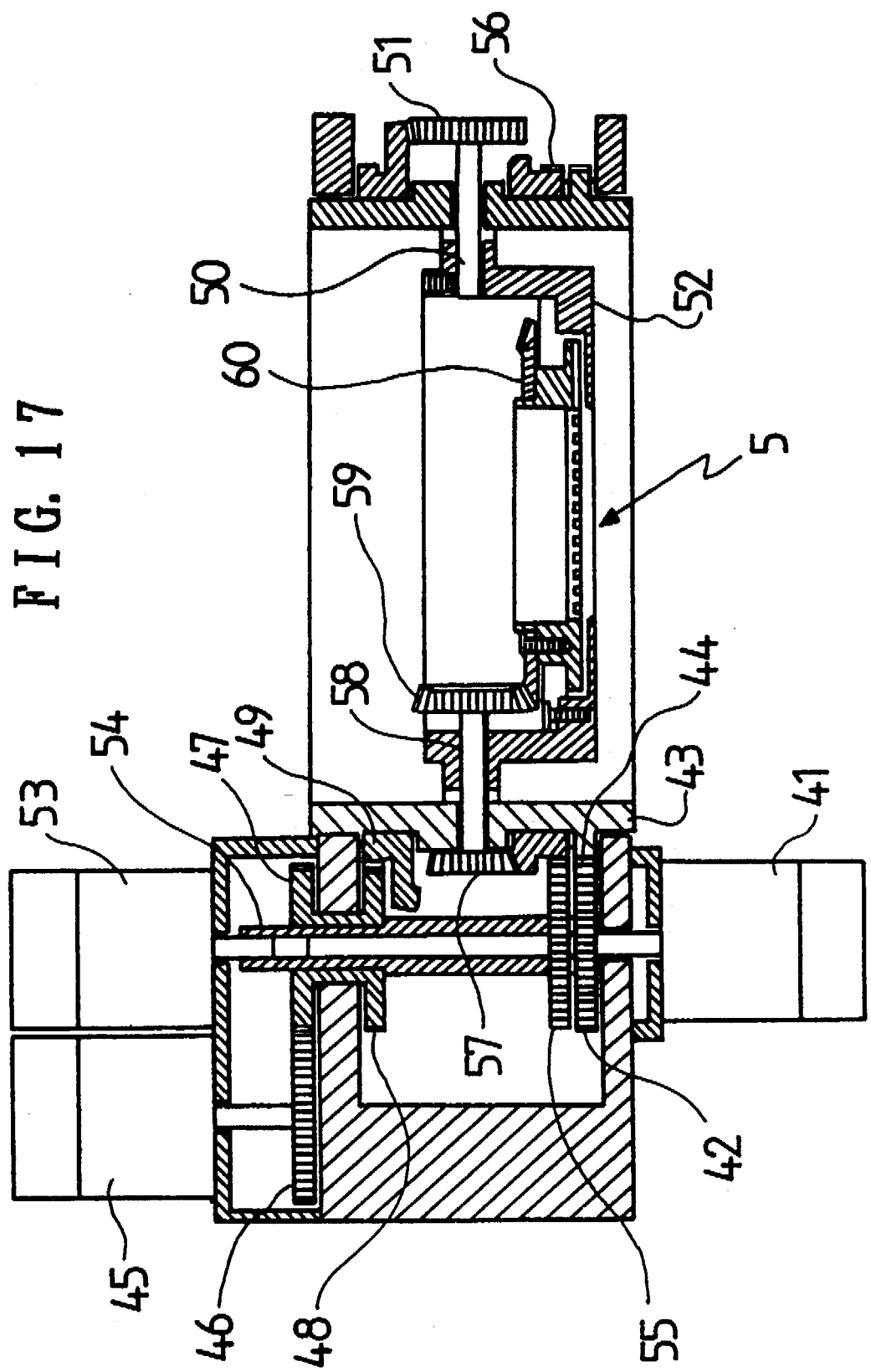
Figure 18:
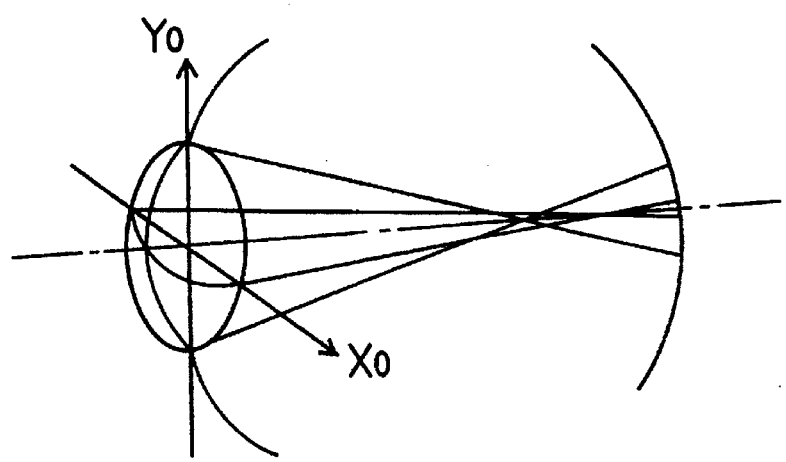
Figure 19:
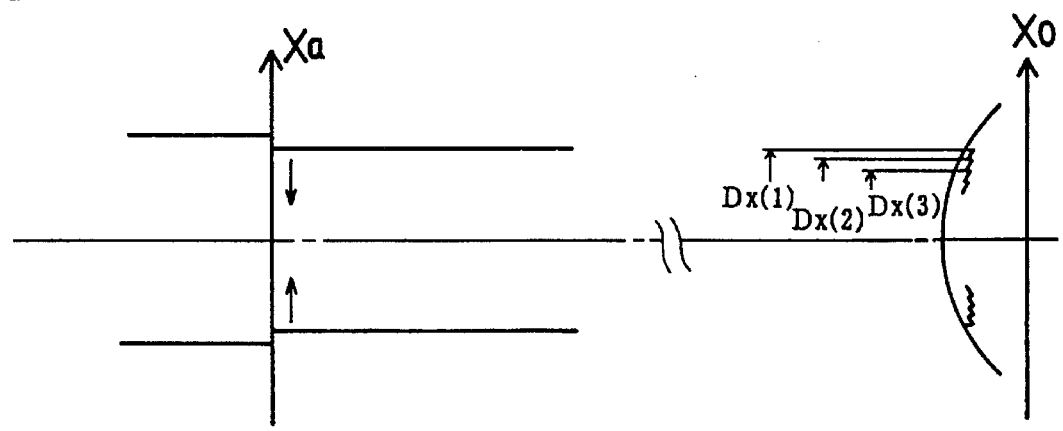
Figure 20:
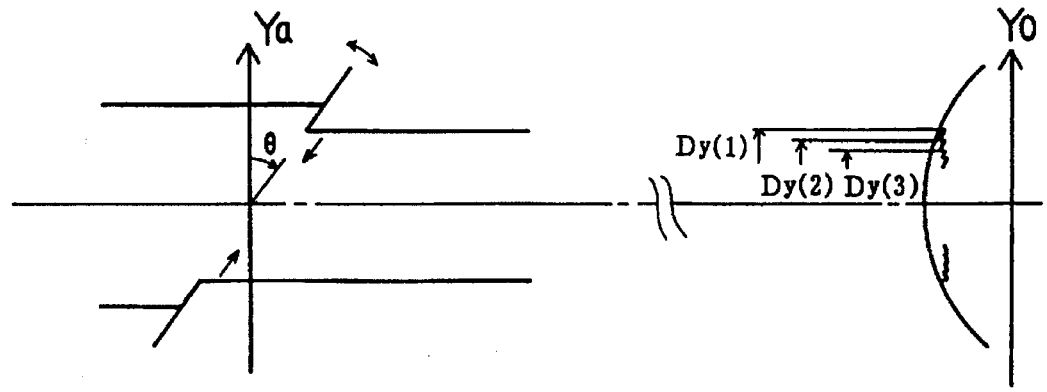
Figure 21:
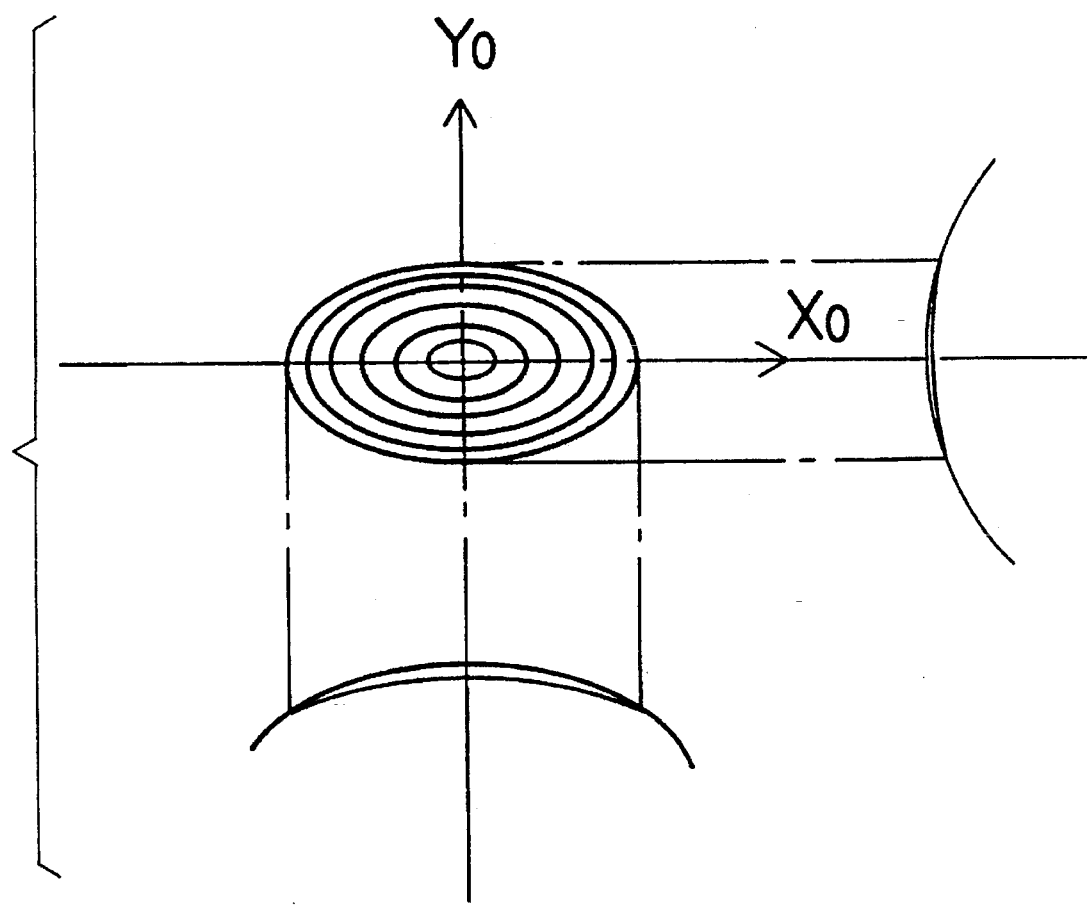

FIGS. 6(a) through 6(d) are diagrams showing the laser beam intensity profile in the vertical (Y-axis) direction on an diaphragm;

FIGS. 7(a) through 7(d) are diagrams showing the laser beam intensity profile in the vertical (Y-axis) direction on the cornea of an eye;

FIGS. 8(a) through 8(e) are diagrams to explain the condition (process) of ablation of FIG. 7;

FIGS. 9(a) and 9(b) are timing charts to explain the movement control of the plane mirror 3 shown in FIG. 4 with respect to the laser pulse;

FIG. 10 is a schematic diagram to explain the ablation of when translational scanning the non-uniform beam;

FIG. 11 is a schematic diagram of the arrangement of components as the modification of the above first embodiment embodying the present invention;

FIG. 12 is a schematic diagram of the arrangement of components of the second embodiment embodying the present invention;

FIG. 13 is a schematic diagram to explain the rotation of the diaphragm;

FIG. 14 is a graph showing the width of the laser beam in Xa-axis direction;

FIG. 15 is a graph showing the width of the laser beam in Ya-axis direction;

FIG. 16 is a schematic front view showing a driving structure of an diaphragm;

FIG. 17 is a schematic sectional view of a driving structure of an diaphragm shown in FIG. 16;

FIG. 18 is a schematic diagram showing one example of a myopic astigmatism;

FIG. 19 is a schematic diagram to explain the condition of correcting in Xo-axis direction;

FIG. 20 is a schematic diagram to explain the condition of correcting in Yo-axis direction;

FIG. 21 is a schematic diagram to explain the condition of correcting a myopic astigmatism.

DETAILED DESCRIPTION OF THE PREFERRED EMBODIMENTS

A detailed description of one preferred embodiment of an apparatus embodying the present invention will now be given referring to the accompanying drawings.

As shown in FIG. 4, an optical system of the ablation apparatus includes a laser source 1 (preferably an excimer laser), plane mirrors 2, 3, and 7 for deflecting laser beam $L_B$ emerging from the laser source 1, a diaphragm 5 with a variable diameter located in the optical path between the mirrors 3, and 7, and a projection lens 6 for projecting the laser beam $L_B$ passing through the diaphragm 5 to a cornea via mirror 7.

The laser beam $L_B$ emerging from the laser source 1 is deflected 90° by the plane mirror 2 and another 90° by the mirror 3 while it remains in the same plane. After the laser beam passes through the diaphragm 5, the laser beam $L_B$ is also deflected 90° by the plane mirror 7 in the same plane, and projected to the surface of the cornea 8.

Image rotator 4, arranged in the above optical system between the mirror 3 and the diaphragm 5, controls the laser beam emitted from the laser source 1 to rotate around or about the optical axis.

Although the laser beam is diffused when passing through the diaphragm 5, it becomes condensed by the projection lens 6. The projection lens 6 is conjugated with the diaphragm 5 and the cornea 8, and the laser beam passing through the aperture confined by a diaphragm 5 is projected on the surface of the cornea 8 such that an ablation area of the cornea is confined.

The cornea 8, being observed by the observing system (not shown), is provided at a position having a predetermined positioning relation for the apparatus and fixed thereon.

Scanning to ablate a uniform depth is explained as follows.

The beam section profile of the laser beam emitted from the laser source 1 of FIG. 5, has an almost uniform intensity distribution F(W) in the horizontal direction (X-axis direction) of the laser beam, but the beam intensity distribution in the vertical direction (Y-axis direction) is a Gaussian distribution F(H).

The plane mirror 3 of FIG. 4, is movable parallel to the Z-axis by a drive motor 9, and the position of the mirror 3 (amount of movement) is detected by a positioning detector 10. The positioning detector 10 may comprise, for example, a rotary encoder attached to a driving axis of the mirror's driving motor 9.

The positioning detector 10 and the laser source 1 are connected to a control device 11, and the laser pulses are emitted based on an output signal of the positioning detector 10. Connected with the control device 11, rotator drive device 12 controls the rotator 4 to rotate based on the output signal from the control device 11, and also diaphragm drive device 13 controls the diaphragm 5 to change its aperture diameter based on the signal from the control device 11. The operation of the present apparatus is controlled by a microcomputer of the control device 11.

As described above, the mirror 3 moves parallel to the Z-axis direction of FIG. 4, whereby the laser beam is moved in parallel in the direction of the Gaussian distribution. The plane mirror 3 moves synchronously to the laser pulse outputted by laser source 1, and after one or more laser pulses have been outputted at a certified position of the plane mirror 3, the mirror 3 moves to a next position, and again at that position of the mirror 3 one or more laser pulses will be further outputted as the mirror 3 moves further to a next position. This moving operation is repeated from the one end of the diaphragm 5 to the other end. This means that the irradiation of the laser beam is repeated on the ablation area of the cornea 8 at a determined interval (by one or more of the laser pulses) so that the pulses are combined and a uniform depth of ablation is achieved.

The moving amount of the plane mirror 3 is determined by correlation among several components, e.g., the depth of ablation, the degree of uniformity required or the intensity and intensity distribution of the laser beam and the like. The adjustment of the laser beam's intensity or the ablation's depth per one pulse may be obtained by adjusting the output power of the laser source within a certain range.

For convenience of explanation, it may be assumed that the plane mirror 3 moves for every pulse although such a one-to-one relationship is not required for the present invention. FIGS. 6(a) through 6(d) show the change of the intensity distribution of the laser beam in Y-axis direction on the diaphragm 5. FIGS. 7(a) through 7(d) show the change of the intensity distribution in the Y-axis direction on the cornea 8. FIGS. 8(a) through 8(e) show the condition (process) of the ablation on the cornea.

When a first pulse of the laser beam having the intensity distribution shown in FIG. 6(a) on the diaphragm 5 is irradiated on the cornea 8 by the projection lens 6, the intensity distribution on the cornea 8 is as shown in FIG. 7(a). At that time, the cornea 8 is ablated by the irradiation of the laser beam, as shown with oblique lines in FIG. 8(a). When a second pulse of the laser beam is irradiated, as the plane mirror 3 has been moved in the Z-axis direction, the intensity distribution on the diaphragm 5 is changed as shown in FIG. 6(b). Accordingly, the intensity distribution projected on the cornea 8 by the projection lens 6 is as shown in FIG. 7(b), and the cornea 8 is further ablated as shown with oblique lines in FIG. 8(b). The third pulse of the laser beam produces an intensity distribution on the diaphragm 5 as shown in FIG. 6(c) and the intensity distribution on the cornea 8 as shown in FIG. 7(c), whereby the area of the cornea shown with oblique lines in FIG. 8(c) is further ablated. Similarly, fourth and subsequent laser pulse up to the n-th pulse of the laser beam, cause intensity distribution on the diaphragm 5 as shown in FIG. 6(d). FIG. 7(d) shows the intensity distributions on the cornea 8 and the area shown in FIG. 8(d) with oblique lines is ablated.

By moving the plane mirror 3 in parallel to the Z-axis direction synchronously with respect to the laser pulse and irradiating the laser beam while scanning it in the direction of its non-uniform intensity distribution, the cornea 8 is ablated with an almost uniform depth.

FIGS. 9(a) and 9(b) are timing charts to explain the timing of a control mechanism that moves the plane mirror 3 synchronously with respect to the laser pulses. In the FIG. 9(a), the output pulse of the laser beam is shown and FIG. 9(b) shows output signals of the detector 10 detecting the position of the plane mirror 3.

The amount of movement of the plane mirror 3 to obtain a uniform ablation depth employs an m-pulse output signal of the position detector 10.

If the output signal of the position detector 10 detecting the position of the plane mirror 3 at the time of the first laser beam pulse is the first detecting pulse, the plane mirror 3 is moved so that the m+1—th output signal is outputted at the time of the second laser pulse and 2 m+1–th output signal is outputted at the time of the third laser pulse so that the laser pulse is emitted each m–th pulse of the output signal of the position detector 10. By repeating such laser beam pulses, uniform ablation by the laser beam irradiation is accomplished.

Figure 1:
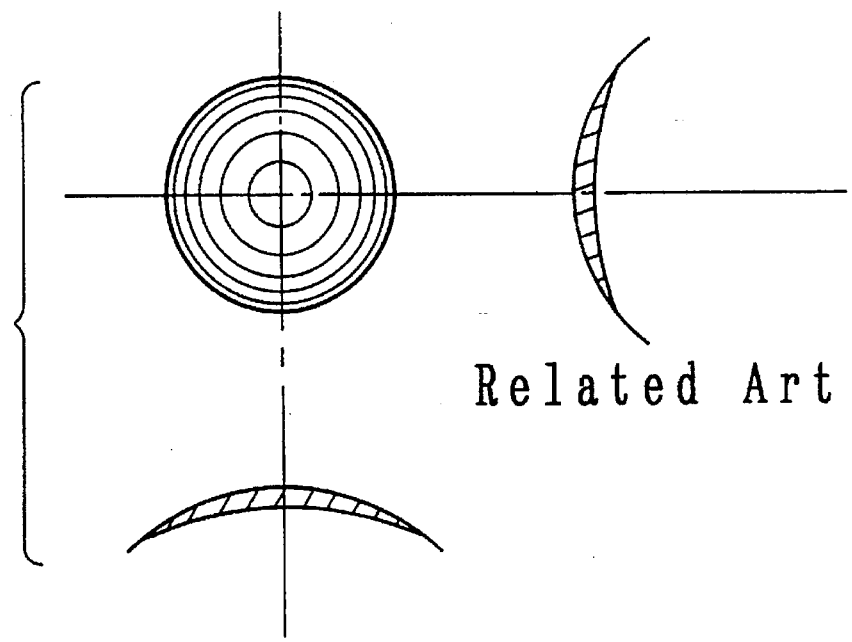
FIG. 1 is a schematic diagram to explain the condition of correcting the myopia in a related art.
Figure 2:
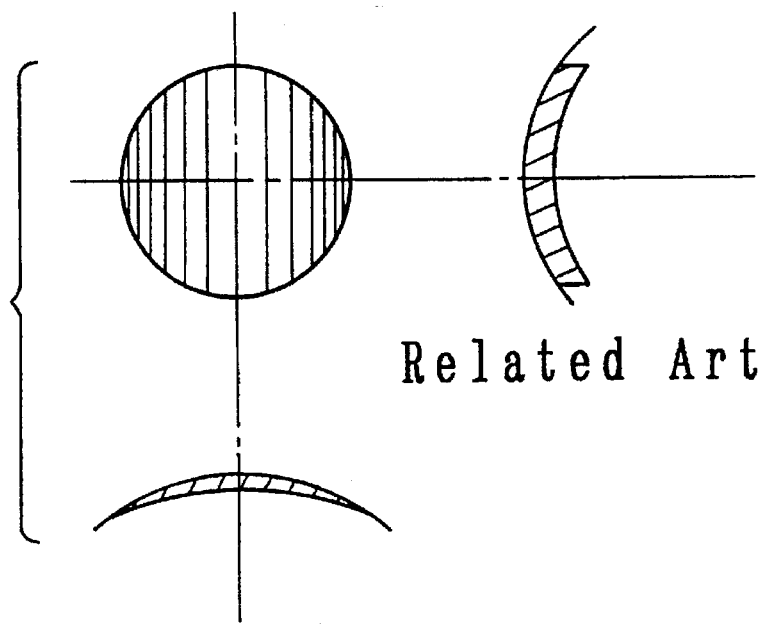
FIG. 2 is a schematic diagram to explain the condition of correcting the astigmatism axis in a related art.
Figure 3:
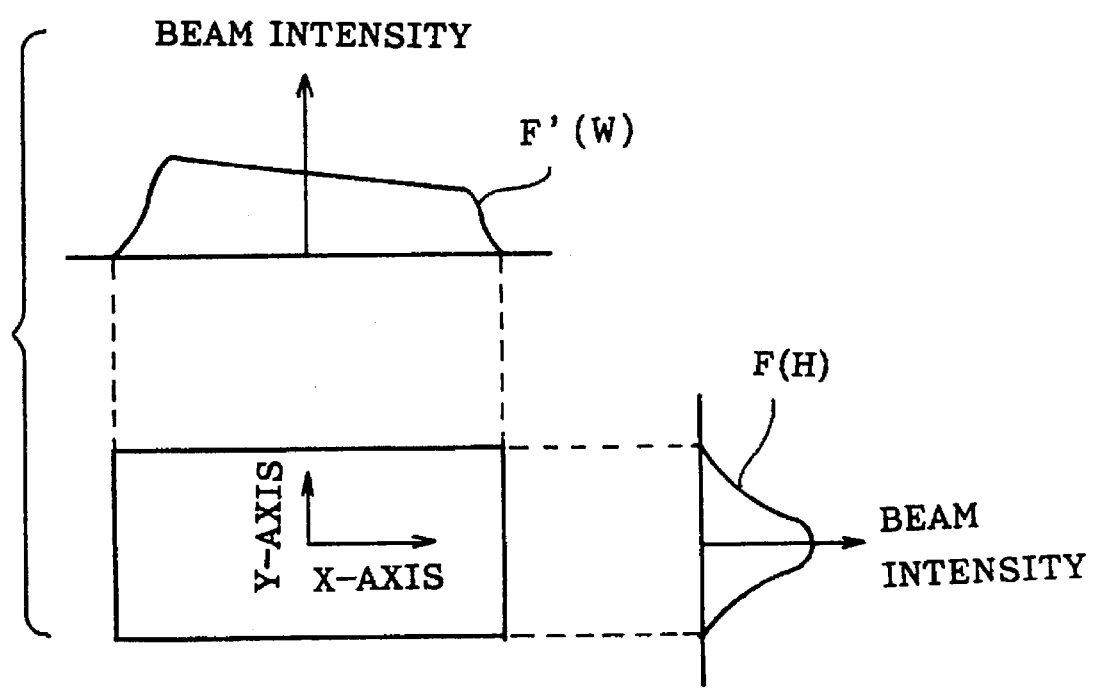
FIG. 3 is a schematic diagram showing one non-uniform beam intensity distribution.

When the intensity distribution F(W) of the laser beam in X-axis direction is not uniform, for example, one side having the intensity being more intense than other side as F'(W) shown in FIG. 3, although an almost uniform depth of ablation is obtained in a translational scanning direction (Y-axis direction) by scanning the laser beam to ablate, the depth of ablation in the non-scanned direction (X-axis direction) is inclined according to the intensity distribution F'(W), that is, deeper in a side of light intensity being more intense. Repeating such scanning causes height-difference between a shallow side and a deep side of the ablation.

Therefore, the image rotator 4 controls a translational scanning direction of the laser beam to rotate per one scanning so as to change the direction of ablation depth inclining, so that the uniform depth is obtained without extreme inclination to one side.

In tests sufficient effect was obtained for operation of the cornea by setting the scanning direction at three directions 120 degrees apart from each other, and further changing the scanning direction in order per scanning.

The rotation angle of the scanning direction is determined in consideration of an extent of uniformity of an ablation to be requested, a number of repeat scanning, and a degree of deflection of intensity distribution or the like. As mentioned above, compared with an ablation by only translational scanning, the deflection of the intensity distribution occurred by an individual difference of the laser oscillator is corrected by rotating the translational scanning direction, whereby the cornea is ablated with an uniform depth.

The present apparatus is controlled by a microcomputer based on the correcting data inputted with keyboard or the like.

The words that show direction in the above description of the first embodiment, are used only to describe a relation of the direction of the laser beam's energy distribution, and other directions may be employed.

In the above embodiment, although an ablation area is confined by projecting a diaphragm 5 on the cornea 8 through a projecting lens 6, it is possible to confine an ablation area by arranging the diaphragm 5 just in front of the cornea 8 as shown in FIG. 11. At that time, it is preferable to put the diaphragm 5 as close as possible to the cornea 8 so as not to be affected by the diffraction, and then to employ the diaphragm 5 formed out of the quality of the material which can keep oculist's visual field, for example clear glasses, so that an observation through a microscope for operation is not obstructed.

As a method to obtain a uniform light distribution, expecting the method of employing the translational scanning mentioned above, arranging a filter which has a constant absorption character into the optical path has been proposed. Although it is not possible to remove individual difference between each of laser oscillators in this method, the present invention may be utilized by rotating pencil rays round the optical axis.

In the following second embodiment, correcting the myopic astigmatism is explained referring to drawings.

In FIG. 12, there is shown an arrangement of an optical system in a second embodiment. The character of the second embodiment consists in the constitution of the diaphragm. The explanation of other part of the constitution is omitted, as it is already explained in the first embodiment.

Diaphragm 5 for confining an ablation area has a variable aperture diameter D as in the first embodiment. The diaphragm 5 can rotate around the optical axis (Z-axis) as shown in FIG. 13, and change the inclination angle to the optical axis around Xa-axis as its center in the vertical plane to the Z-axis. When diaphragm 5 is inclined at an angle $\theta$ around Xa-axis as its center, the width of the laser beam (Wx) in Xa-axis direction passed through the diaphragm 5 is constant regardless of the inclination angle $\theta$, as shown in FIG. 14, and another width of the laser beam (Wy) in Ya-axis direction reduces as an inclination angle $\theta$ extends as shown in FIG. 15.

In FIG. 16 and FIG. 17, a driving constitution of the diaphragm 5 is explained, specifically, FIG. 16 shows a front view and FIG. 17 shows a sectional view of the driving constitution with the diaphragm 5.

As a gear 42 engages with a gear portion 44 formed on the periphery of cylindrical part 43 in which the diaphragm 5 is held, the diaphragm 5 is rotated Pound the optical axis by the rotation of pulse motor 41 through the gear 42.

An inclination angle of the diaphragm 5 to the optical axis round Xa-axis is changed as following constitution.

As a gear 46 rotated by pulse motor 45 rotates a gear 48 through a gear 47, the gear 48 engages with gear 49 which rotates around the cylindrical part 43, so that a gear 49 inclines a small cylindrical part 52 holding the diaphragm through gear 51 connected with a shaft 50.

Changing an aperture diameter of the diaphragm 5 is explained as follows. Rotation of a gear 55 driven by pulse motor 53 through an shaft 54 is conducted to a gear 57 through gear 56 rotating around the cylindrical part 43, further a gear 59 is rotated by the gear 57 through a shaft 58. The diameter of the diaphragm 5 is changed by the gear 59 rotating a diaphragm driving plate 60. In the present embodiment, a diaphragm constitution for changing a diameter of a diaphragm by rotating the diaphragm driving plate 60 is constructed similarly to that of a well-known camera or the like, and so the explanation thereof is omitted.

In the correcting operation of myopic astigmatism, the apparatus mentioned above is operated as follows.

In FIG. 18, the myopia of an eye to be corrected has also the astigmatism (regular astigmatism). When the minor principal meridian direction of the eye is $X_o$-axis and the major principal meridian direction is $Y_o$-axis, the diaphragm 5 is rotated round the optical axis by the pulse motor 41 so that an inclinational rotation axis (Xa-axis) for a center to rotate the diaphragm 5 toward a direction of the optical axis is in agreement with the minor principal meridian direction ($X_o$-axis) of the eye. Further, the major principal meridian direction of the eye. ($Y_o$-axis) is in agreement with the Ya-axis of the diaphragm 5.

Control of the an aperture diameter D of the diaphragm 5 is as follows. Referring to FIG. 19, diameter D of the diaphragm 5 is controlled to change the beam width into Dx(1), Dx(2), Dx(3) . . . Dx(n) so that the myopia in the minor principal meridian direction ($X_o$-axis) of the eye could be corrected. Therefore, the surface of the cornea can be ablated so that the curvature of the cornea in the $X_o$-axis direction have a desired curvature radius.

In synchronizing with controlling the aperture diameter D of the diaphragm 5, inclining movement of the diaphragm 5 around Xa-axis as its center is controlled according to the degree of astigmatism of an eye. By inclining the diaphragm, although the width of laser beam (Wx) in the Xa-axis direction is constant as shown in FIG. 14, the width (Wy) in the Ya-axis direction changes as shown in FIG. 15. Therefore, the inclination angle θ of the diaphragm 5 is controlled so that a curvature of the cornea in $Y_o$ -axis direction could have a desired radius of curvature by changing the beam width into Dy(1), Dy(2), Dy(S), . . . Dy(n) as shown in FIG. 20.

The inclination angle of the diaphragm 5 as mentioned above is controlled through a microcomputer of the apparatus based on ablation data inputted thereinto with a keyboard or the like.

As mentioned above, in synchronizing with controlling a inclination angle θ and an aperture diameter D of the diaphragm 5 by pulse motor 45, 53, the surface of the cornea is ablated elliptically by irradiating the laser beam so that each curvature in the major principal meridian direction and in the minor principal meridian direction of the eye has desired curvature. Therefore, the myopic astigmatism is corrected.

In the present embodiment mentioned above, although an aperture diameter D of the diaphragm is controlled so as to reduce its size from larger to smaller, it is possible to change the aperture diameter D reversely from smaller to larger. Further, instead of rotating the diaphragm 5 around the optical axis, it is also possible to rotate an image rotator around an optical axis of a laser beam.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claim is:

1. An apparatus for operating on a cornea using a laser beam to correct a refractive error of an eye, comprising:

a laser source for emitting a laser beam along an optical path, the laser beam having a non-uniform beam intensity distribution along a first axis and a uniform beam intensity along a second axis;

an optical system for irradiating the laser beam from the laser source onto a surface of the cornea, said optical system Comprising an ablation area confining means;

scanning means for scanning the laser beam along the first axis;

beam rotating means for rotating the laser beam about the optical path; and control means for controlling the beam rotating means whenever the laser beam is scanned by the scanning means;

wherein the laser beam is rotated at substantially equal angular intervals, several times each ablation area confined by the ablation area confining means so as to ablate the cornea a uniform depth.

2. The apparatus according to claim 1, wherein the beam rotating means comprises an image rotator.

3. The apparatus according to claim 2, wherein the control means controls the image rotator to rotate about the optical path at a set angle whenever the laser beam is scanned by the scanning means.

4. The apparatus according to claim 1, wherein the ablation area confining means comprises a diaphragm having a variable aperture diameter.

5. The apparatus according to claim 4, further comprising projecting means arranged in the optical system for conjugate positioning of the diaphragm in relation with the cornea of the eye.

6. The apparatus according to claim 4, further comprising diaphragm rotating means for rotating the diaphragm about the optical path; and changing means for changing an inclination angle of the diaphragm to the optical axis.

7. The apparatus according to claim 1, wherein the scanning means comprises a reflection-type optical element for reflecting the laser beam; and moving means for moving the reflection-type optical element along the first axis.

8. The apparatus according to claim 7, further comprising position detecting means for detecting the position of the reflection-type optical element; and control means for controlling the laser source in response to the position detecting means.

9. An apparatus for operating on a cornea using a laser beam to correct a refractive error of an eye, comprising:

a laser source for emitting a laser beam;

an optical system for irradiating the laser beam onto the cornea of the eye, said optical system comprising an ablation area confining means;

correcting means correcting a difference in ablation: depth based on a non-uniform intensity distribution peculiar to the laser beam in an ablation area confined by the ablation area confining means; and beam rotating means for rotating the laser beam having a corrected intensity distribution about an optical axis in the optical system;

wherein the laser beam is rotated at substantially equal angular interval, several times each ablation area confined by the ablation area confining means so to ablate the cornea a uniform depth.

10. The apparatus according to claim 9, wherein the laser source emits a laser beam having a non-uniform beam intensity distribution in a first direction and a uniform beam intensity distribution in a second direction, and the correcting means comprises a translational scanning means for scanning the laser beam in the first direction.

11. The apparatus according to claim 9, wherein the beam rotating means comprises an image rotator.

12. The apparatus according to claim 9, further comprising ablation repeating means for repeating an ablation of predetermined depth on the cornea by repeating a step for irradiating the laser beam having a corrected intensity distribution onto the cornea of the eye through the optical system.

13. The apparatus according to claim 12, further comprising controlling means for controlling the beam rotating means when repeating the ablation by the ablation repeating means.

14. An apparatus for operating on a cornea using a laser beam to correct a refractive error of an eye, comprising:

a laser source for emitting a laser beam;

an optical system for irradiating the laser beam onto the cornea of the eye;

a circular diaphragm, arranged in the optical system, for confining an ablation area;

changing means for changing an aperture diameter of the ablation area confined by the circular diaphragm;

diaphragm inclining means for inclining the circular diaphragm relative to an optical axis of the laser beam; and changing means for changing the angle of the principal meridians of an ellipse confined by the circular diaphragm inclined by said diaphragm inclining means.

15. The apparatus according to claim 14, wherein the laser beam has a non-uniform intensity distribution in a first direction and a uniform beam intensity distribution in a second direction; and the apparatus further comprising:

scanning means for scanning the laser beam in the first direction;

beam rotating means for rotating the laser beam about the optical axis; and beam rotation control means for controlling the beam rotating means whenever the laser beam is scanned in the first direction.

16. The apparatus according to claim 15, wherein the beam rotating means comprises an image rotator.

17. An apparatus for operating on a cornea using a laser beam to correct a refractive error of an eye, comprising:

a laser source for emitting a laser beam;

an optical system for irradiating the laser beam onto the cornea of the eye;

a circular diaphragm, arranged in the optical system, for confining an ablation area on the cornea;

diaphram rotating means for rotating the diaphragm about an optical axis;

changing means for changing an aperture diameter of the diaphragm;

diaphragm inclining means for inclining the diaphragm with respect to an optical axis of the laser beam; and changing means for changing the angle of the principal meridians of an ellipse confined by the circular diaphragm inclined by said diaphragm inclining means.

18. The apparatus according to claim 17, wherein the laser beam has a non-uniform intensity distribution in a first direction and a uniform beam intensity distribution in a second direction; and the apparatus further comprising;

scanning means for scanning the laser beam in the first direction;

beam rotating means for rotating the laser beam about the optical axis; and beam rotation control means for controlling the beam rotating means whenever the laser beam is scanned in the first direction.

19. The apparatus according to claim 18, wherein the beam rotating means comprises an image rotator.

* * * * *